United States Patent [19]

Fahmy

[11] 4,391,760
[45] Jul. 5, 1983

[54] S-(TERTIARY ALKYL) ALKYLPHOSPHONOTHIOIC HALIDES

[75] Inventor: Mohamed A. Fahmy, Princeton, N.J.

[73] Assignee: Rhone-Poulenc Agrochimie, Lyons, France

[21] Appl. No.: 221,642

[22] Filed: Dec. 31, 1980

[51] Int. Cl.³ .............................................. C07F 9/20
[52] U.S. Cl. .................................... 260/961; 260/973
[58] Field of Search ......................................... 260/960

[56] References Cited

U.S. PATENT DOCUMENTS 3,149,143 9/1964 Newallis et al. ..................... 260/960
3,346,669 10/1967 Regel .................................. 260/960

FOREIGN PATENT DOCUMENTS 25270 3/1981 European Pat. Off. ............ 260/960

OTHER PUBLICATIONS

Kosolapoff et al., "Organic Phosphorus Compounds", vol. 7, (1976), pp. 41-42.
Akamsin et al., "C.A.", vol. 68, (1968), #29783x.

Primary Examiner—Anton H. Sutto
Attorney, Agent, or Firm—Burns, Doane, Swecker & Mathis

[57] ABSTRACT

Compounds useful as intermediates for insecticides and nematocides having the formula

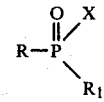

in which
R is an alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is tertiary alkyl of 4 to 8 carbon atoms; and
X is halogen
are disclosed as well as their preparation by direct reaction of an alkylphosphonic dihalide with a tertiary-alkyl thiol.

6 Claims, No Drawings

S-(TERTIARY ALKYL) ALKYLPHOSPHONOTHIOIC HALIDES

CROSS-REFERENCE TO RELATED APPLICATIONS

Branched S-alkyl alkylphosphonodithioc halides and the method of their preparation are disclosed in U.S. patent application Ser. No. 71,465, filed Aug. 31, 1979 by Mohamed A. Fahmy, and subsequently abandoned in favor of continuation application Ser. No. 201,937, filed Oct. 29, 1980, allowed Apr. 23, 1982.

SUMMARY OF THE INVENTION

This invention relates to the process of preparation of compounds of the formula

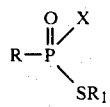

by reaction of

with $R_1SH$ in a solvent, at a temperature of about 20° C. to 100° C. in the presence of a base; in which R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;

$R_1$ is tertiary alkyl of 4 to 8 carbon atoms; and

X is halogen.

The compounds of this invention are useful as intermediates for the production of valuable insecticides and nematocides as described in more detail hereinafter.

DETAILED DESCRIPTION OF THE INVENTION

This invention relates to a simple process for the production of S-(tertiary alkyl) alkylphosphonothioic halides by the direct addition of thiols to alkylphosphonic dihalides.

The synthesis of S-alkyl alkylphosphonothioic halides is usually accomplished by methods other than the direct addition of thiols to alkylphosphonic dihalides because direct reaction is normally accompanied by an undesirable side reaction in which both halo atoms in the phosphonodihalide are substituted with the alkyl thiol. The side reaction is a particular problem where normal alkyl thiols are used. Thus, when the synthesis of normal S-alkyl alkylphosphonothioic chlorides is desired, alternative routes are selected.

I have discovered that tertiary alkylthiols react smoothly with alkylphosphonic dichloride to give mono addition of one thiol in good yield, according to the following equation:

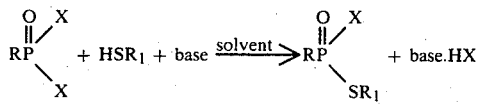

In the above formulae:

R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms. Preferably, R is alkyl, particularly methyl or ethyl;

$R_1$ is tertiary alkyl of 4 to 8 carbon atoms, preferably tert-butyl or tert-amyl; and X is halogen, particularly chlorine.

Suitable reaction solvents include water and organic solvents. With water the base is advantageously an inorganic base such as sodium hydroxide. With organic solvents the base is advantageously a tertiary amine such as trimethylamine, triethylamine, pyridine, dimethyl aniline or diethyl aniline.

Suitable organic solvents include benzene, toluene, cyclohexane, acetone and 2-butanone.

Generally, the reaction is conducted at a temperature of between about 20° C. to 100° C., but the temperature is not critical except insofar as it is sufficient to make the reaction proceed at a reasonable rate and is not excessive. It has been found advantageous to add the tertiary amine to the other reactants at a temperature of about 20° C. to 30° C. and then to heat the entire reaction mixture to a temperature of about 70° C. to 80° C. to complete the reaction.

The reaction is normally carried out with an approximately equal molar ratio of the alkyl phosphonic dihalide, thiol and the base. An excess of about 10 to 20% of the alkylphosphonic dihalide can be used relative to the other reactants. However, the use of a slight excess of the thiol and the base relative to the alkylphosphonic dihalide (5–10% excess) did not appreciably affect the yield.

The above compounds find particular utility as intermediates for preparation of compounds which are useful, for example, in the control of Corn rootworm and which exhibit long residual soil activity. Example 2 illustrates a compound useful for the control of corn rootworm and its preparation from an intermediate resulting from the claimed process. More detailed information regarding the utility of the compounds prepared by the claimed process appears in copending applications of Mohamed A. Fahmy entitled "O-ALKYL S-(TERTIARY ALKYL) ALKYLPHOSPHONOTHIOATE INSECTICIDES AND NEMATOCIDES" filed Nov. 21, 1980 as U.S. application Ser. No. 209,093, and subsequently abandoned in favor of continuation application Ser. No. 359,356, filed Mar. 18, 1982, now pending; and "O-ARYL S-(TERTIARY ALKYL) ALKYLPHOSPHONOTHIOATE INSECTICIDES AND NEMATOCIDES" filed Nov. 21, 1980 as U.S. application Ser. No. 209,094, and subsequently abandoned in favor of continuation application Ser. No. 369,555, filed Apr. 19, 1982, now pending; which applications are incorporated herein by reference.

The following examples illustrate the process of this invention and the method of converting the intermediates of this invention into useful insecticides.

EXAMPLE 1

S-tert-butyl ethylphosphonothioic chloride $$\text{CH}_3\text{CH}_2-\overset{\overset{\displaystyle O}{\|}}{\underset{\underset{\displaystyle \underset{\displaystyle \text{CH}_3}{|}}{\text{S}-\overset{\displaystyle \text{CH}_3}{\underset{\displaystyle |}{\text{C}}}-\text{CH}_3}}{\text{P}}}\diagup\text{Cl}$$

To a solution of ethylphosphonic dichloride (32.0 g, 0.22 mol) in 300 ml of toluene, was added 2-methyl-2-propanethiol (18 g, 0.2 mol). While stirring triethylamine (22 g, 0.22 mol) was added dropwise and the temperature of the reaction was maintained at 30°–35° C. during the addition of the amine. After the complete addition of the amine, the mixture was stirred overnight at room temperature. The amine hydrochloride was filtered and the toluene solution was concentrated under vacuum. Hexane (200 ml) was added and the solution was filtered again.

The solvents were stripped off under vacuum and the residual liquid was distilled. The product (25 g, 72.5% yield) distilled at 72°–73° C./0.7 mm. $^1$H-NMR in chloroform-d-Si(Me)$_4$ confirmed the structure of the title compound.

EXAMPLE 2

This example illustrates the utility of a compound of this invention as an intermediate in the synthesis of an insecticide and nematocide.

O-phenyl S-tert-butyl ethylphosphonothioate

To a solution of S-tert butyl ethylphosphonothioic chloride (5 g, 0.025 mol), and phenol (2.35 g, 0.025 mol) in 20 ml acetone, was added, in one portion, triethylamine (2.5 g, 0.025 mol). The mixture was stirred overnight under nitrogen at room temperture. The reaction mixture was diluted with toluene (100 ml) and washed once with 5% NaOH solution, and twice with water. The solution was dried over anhydrous sodium sulfate and the solvent was stripped off under vacuum. The residual liquid was subjected to high vacuum (0.2 mm) at 60° C. for 15 minutes to yield the desired product as confirmed by $^1$H-NMR spectrum in chloroform-d-Si(Me)$_4$.

EXAMPLE 3

S-tert-amyl ethylphosphonothioic chloride

In a manner similar to that of Example 1, 2-ethyl-2-propanethiol was reacted with ethylphosphonic dichloride to obtain the title compound.

I claim:

1. A compound of the formula $$R-\overset{\overset{\displaystyle O}{\|}}{\underset{\displaystyle SR_1}{P}}\diagup X$$

wherein R is alkyl of 1 to 8 carbon atoms, R$_1$ is tertiary alkyl of 4 to 8 carbon atoms and X is halogen.

2. A compound of claim 1 wherein R$_1$ is tert-butyl.
3. A compound of claim 1 wherein R$_1$ is tert-amyl.
4. A compound of claim 1 wherein X is chloro.
5. The compound of claim 1 wherein R is ethyl, R$_1$ is tert-butyl and X is chloro.
6. The compound of claim 1 wherein R is ethyl, R$_1$ is tert-amyl and X is chloro.

* * * * *